(12) United States Patent
Takahashi et al.

(10) Patent No.: US 10,201,461 B2
(45) Date of Patent: Feb. 12, 2019

(54) PANTS-TYPE ABSORBENT ARTICLE

(71) Applicant: LIVEDO CORPORATION, Shikokuchuo-shi, Ehime (JP)

(72) Inventors: Yuki Takahashi, Mima-gun (JP); Emi Amano, Mima-gun (JP); Tomohito Uda, Osaka (JP)

(73) Assignee: LIVEDO CORPORATION, Shikokuchuo-shi (JP)

( * ) Notice: Subject to any disclaimer, the term of this patent is extended or adjusted under 35 U.S.C. 154(b) by 1050 days.

(21) Appl. No.: 14/371,707

(22) PCT Filed: Mar. 28, 2013

(86) PCT No.: PCT/JP2013/002124
§ 371 (c)(1),
(2) Date: Jul. 10, 2014

(87) PCT Pub. No.: WO2013/153756
PCT Pub. Date: Oct. 17, 2013

(65) Prior Publication Data
US 2014/0378934 A1   Dec. 25, 2014

(30) Foreign Application Priority Data

Apr. 12, 2012   (JP) ................. 2012-090709

(51) Int. Cl.
*A61F 13/15* (2006.01)
*A61F 13/20* (2006.01)
*A61F 13/49* (2006.01)

(52) U.S. Cl.
CPC .... *A61F 13/4902* (2013.01); *A61F 13/49011* (2013.01); *A61F 13/49014* (2013.01);
(Continued)

(58) Field of Classification Search
CPC ............. A61F 13/49011; A61F 13/4902
See application file for complete search history.

(56) References Cited

U.S. PATENT DOCUMENTS

| | | | |
|---|---|---|---|
| 6,306,122 B1 | 10/2001 | Narawa et al. | |
| 9,681,998 B2 * | 6/2017 | Nakano | A61F 13/49017 |
| 2003/0066597 A1 * | 4/2003 | Venturino | A61F 13/15699 |
| | | | 156/256 |
| 2003/0217803 A1 | 11/2003 | Hermansson et al. | |

(Continued)

FOREIGN PATENT DOCUMENTS

| | | |
|---|---|---|
| CN | 102196762 A | 9/2011 |
| EP | 2347744 A1 | 7/2011 |

(Continued)

OTHER PUBLICATIONS

International Search Report dated Jun. 27, 2013, issued in corresponding application No. PCT/JP2013/002124.

*Primary Examiner* — Michele M Kidwell
(74) *Attorney, Agent, or Firm* — Westerman, Hattori, Daniels & Adrian, LLP

(57) ABSTRACT

A disposal diaper (1) improves breathability by laminating a folded portion (46) and an opposing portion (47) to form a first waist circumferential region (407), which is an upper portion of a waist circumferential region (406). A second waist circumferential region (408) below the first waist circumferential region is formed by laminating the folded portion, an end sheet (5), a second exterior sheet (42), and the opposing portion, and a second waist elastic member (444) is joined between the folded portion and the end sheet. The folded portion has a horizontal bending resistance of 80 mm or less. This allows the second waist circumferential region to easily contract. The thickness and strength of the second waist circumferential region increase accordingly, and this makes it possible to reduce damage to an exterior sheet (4) in the waist circumferential region.

17 Claims, 12 Drawing Sheets

(52) U.S. Cl.
CPC .......... *A61F 13/49017* (2013.01); *A61F 2013/49022* (2013.01)

(56) References Cited

U.S. PATENT DOCUMENTS

| | | |
|---|---|---|
| 2004/0210205 A1 | 10/2004 | VanGompel et al. |
| 2005/0154367 A1* | 7/2005 | Ikegami ............... A01K 23/00 604/389 |
| 2006/0254708 A1 | 11/2006 | Wada et al. |
| 2006/0264859 A1* | 11/2006 | Tsuji ................ A61F 13/49012 604/385.28 |
| 2008/0134487 A1 | 6/2008 | Hartono |
| 2010/0076394 A1 | 3/2010 | Hayase et al. |
| 2011/0201922 A1 | 8/2011 | Hezemans et al. |
| 2012/0165774 A1 | 6/2012 | Otsubo et al. |
| 2013/0110065 A1 | 5/2013 | Takahashi et al. |
| 2013/0110070 A1* | 5/2013 | Nakaoka ........... A61F 13/49011 604/385.3 |
| 2015/0088087 A1* | 3/2015 | Kawakami ........... A61F 13/496 604/385.16 |
| 2015/0202095 A1* | 7/2015 | Kawakami ........... A61F 13/496 604/385.16 |

FOREIGN PATENT DOCUMENTS

| | | |
|---|---|---|
| JP | 09-038133 A | 2/1997 |
| JP | 11-4853 A | 1/1999 |
| JP | 2001-87314 A | 4/2001 |
| JP | 2006-141642 A | 6/2006 |
| JP | 2006-247009 A | 9/2006 |
| JP | 2008-142342 A | 6/2008 |
| JP | 2008-212232 A | 9/2008 |
| JP | 2009-90029 A | 4/2009 |
| JP | 2009-247418 A | 10/2009 |
| JP | 2010-131167 A | 6/2010 |
| JP | 2010-227654 A | 10/2010 |
| JP | 2011-67602 A | 4/2011 |
| JP | 2011-177285 A | 9/2011 |
| JP | 2011-254996 A | 12/2011 |
| KR | 10-2013-0009880 A | 1/2013 |
| WO | 2008/008140 A2 | 1/2008 |
| WO | 2010/055767 A1 | 5/2010 |
| WO | 2010053006 A1 | 5/2010 |
| WO | 2012/008140 A1 | 1/2012 |

\* cited by examiner

[Fig. 1]
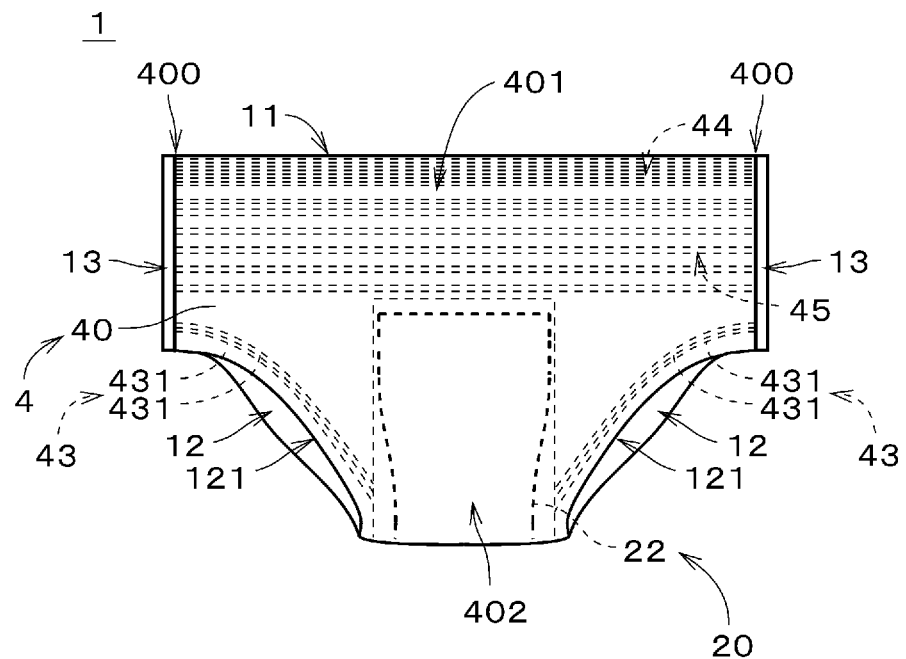
[Fig. 2]
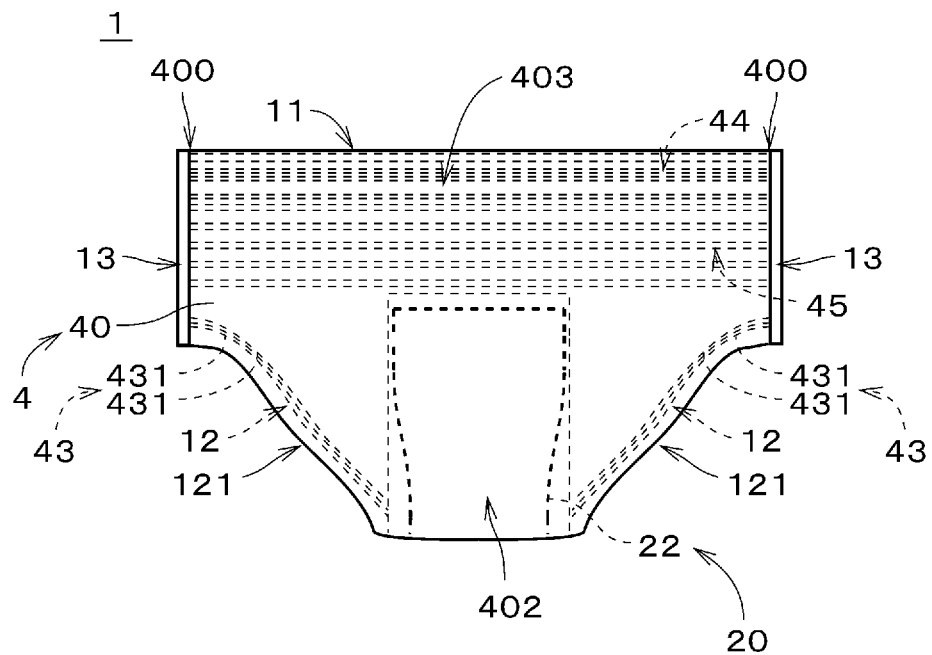

[Fig. 3]
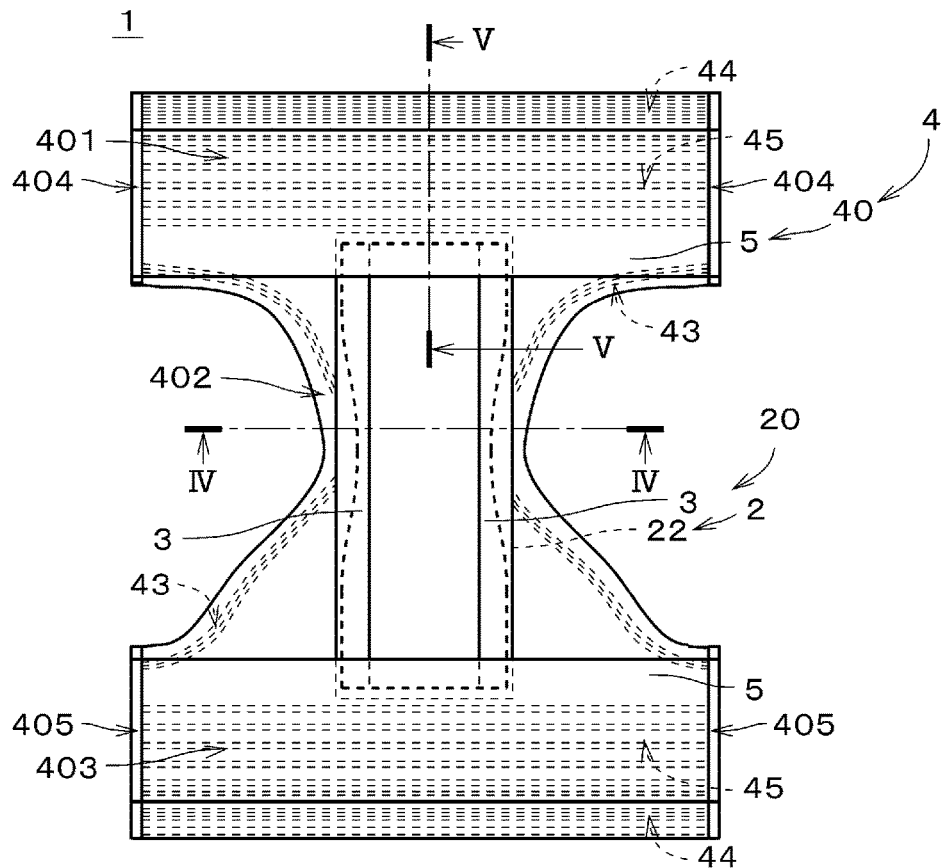
[Fig. 4]
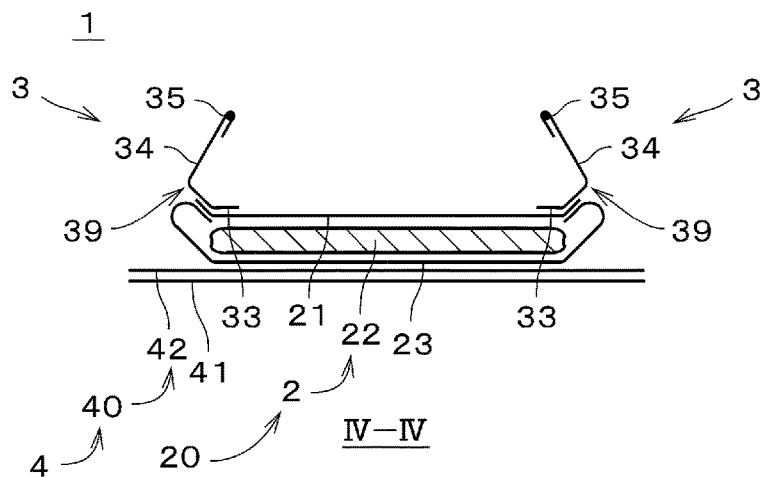
IV—IV

[Fig. 5]
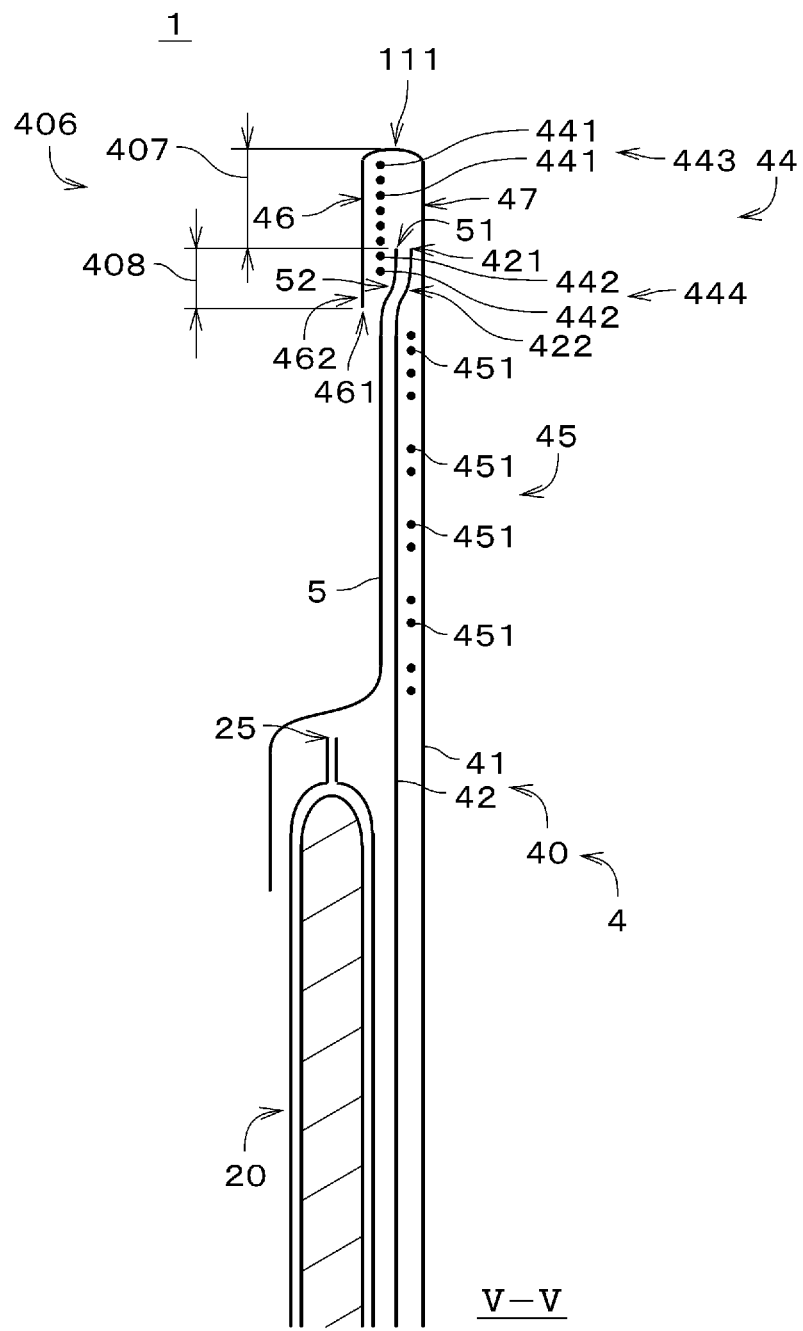

[Fig. 6]
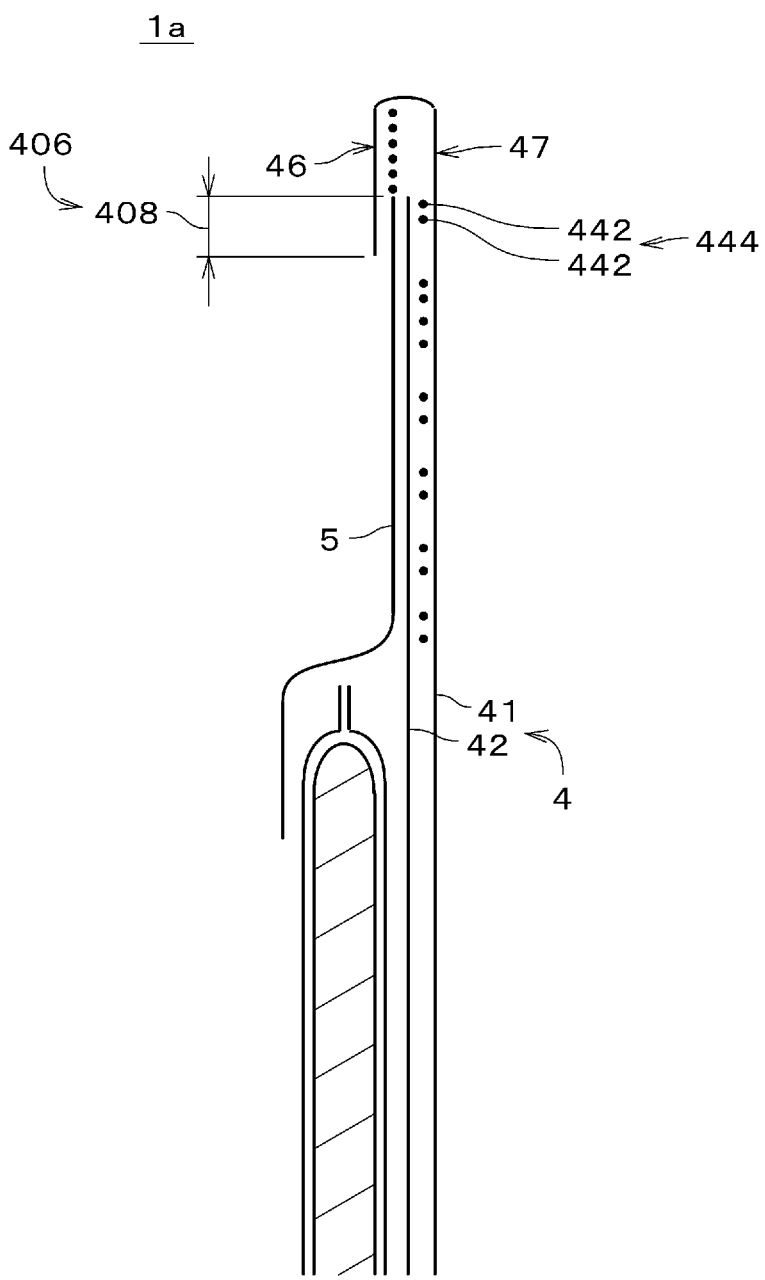

[Fig. 7]
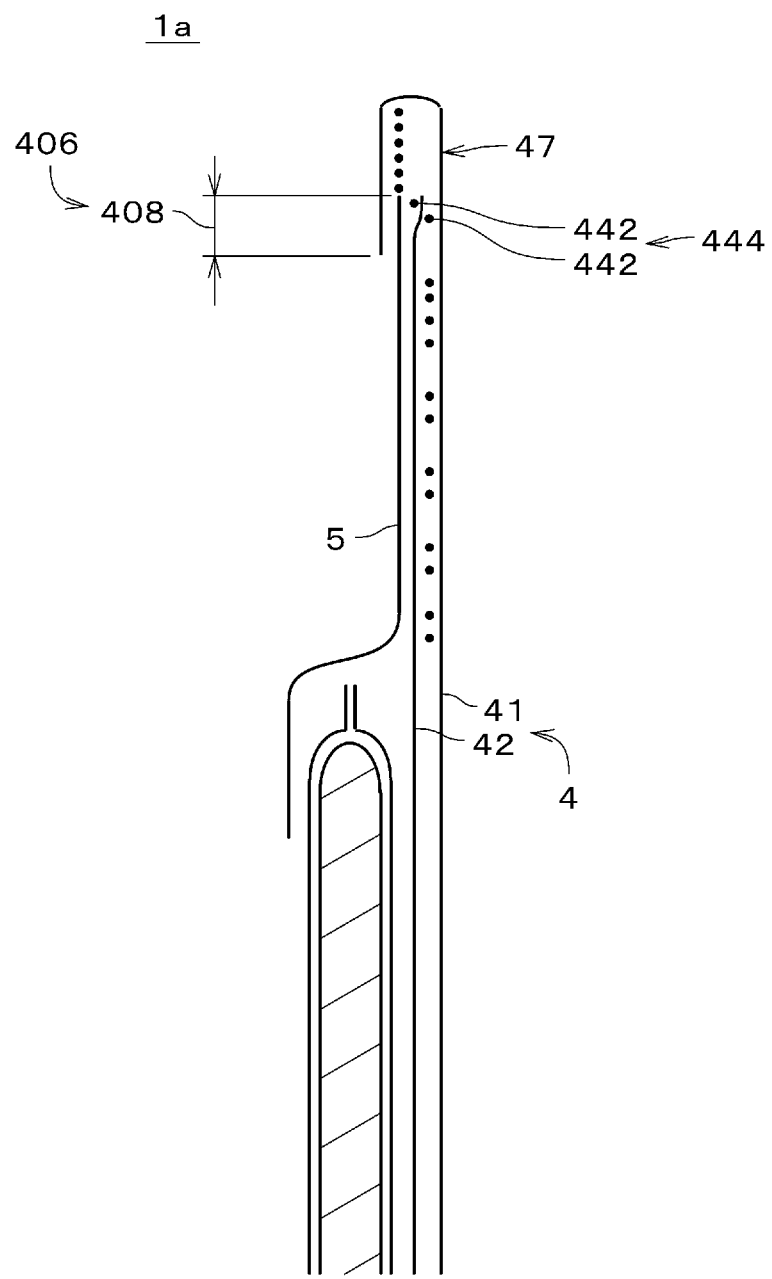

[Fig. 8]
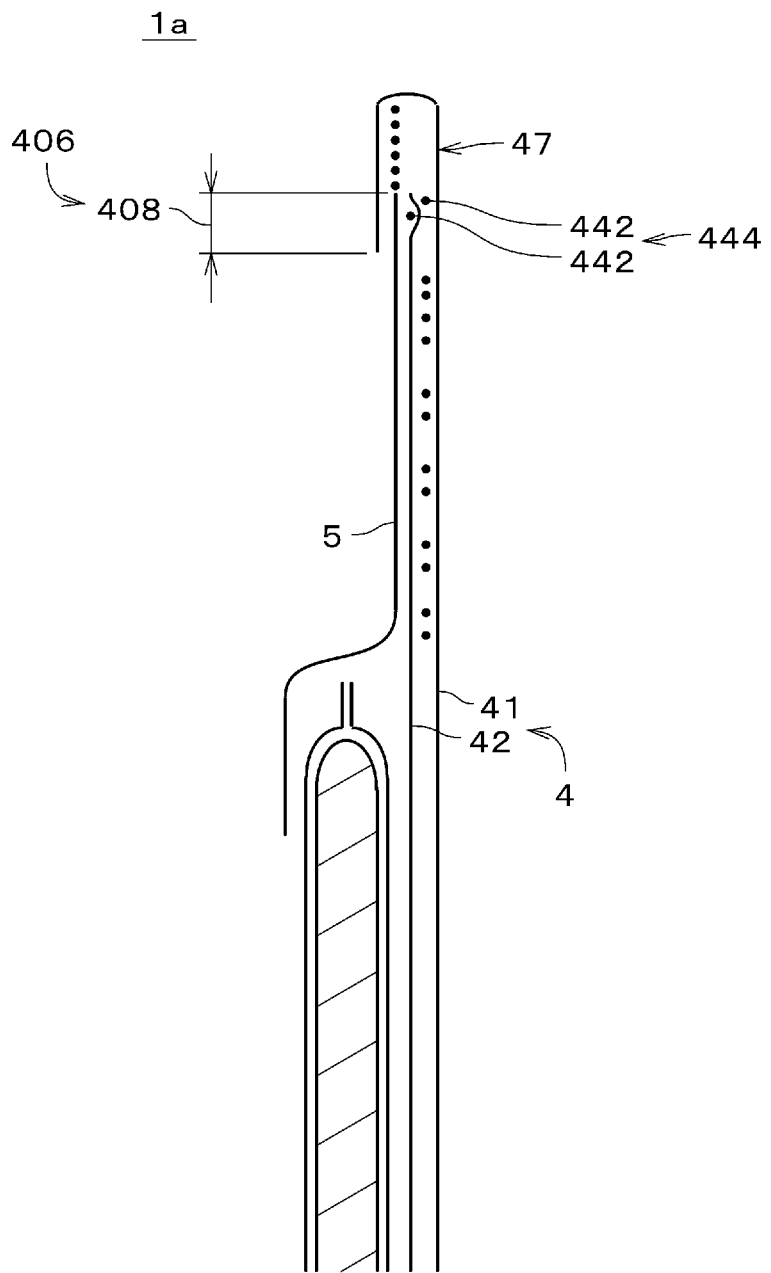

[Fig. 9]
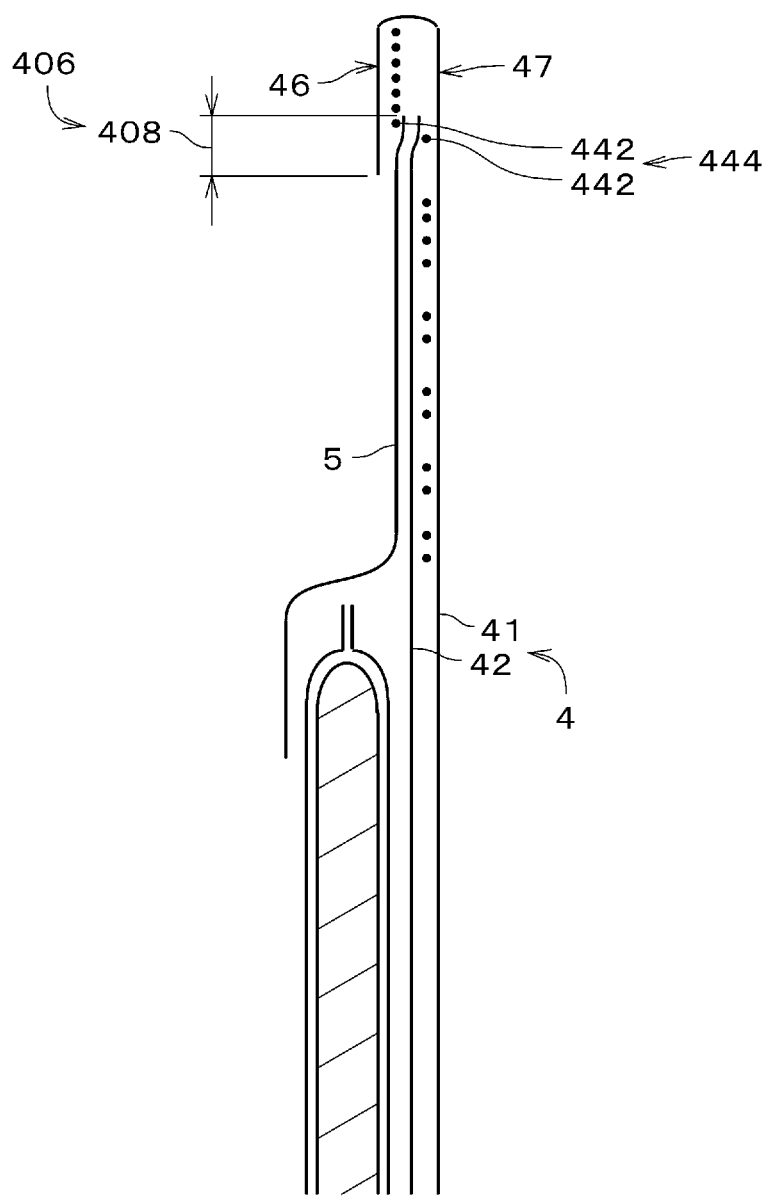

[Fig. 10]
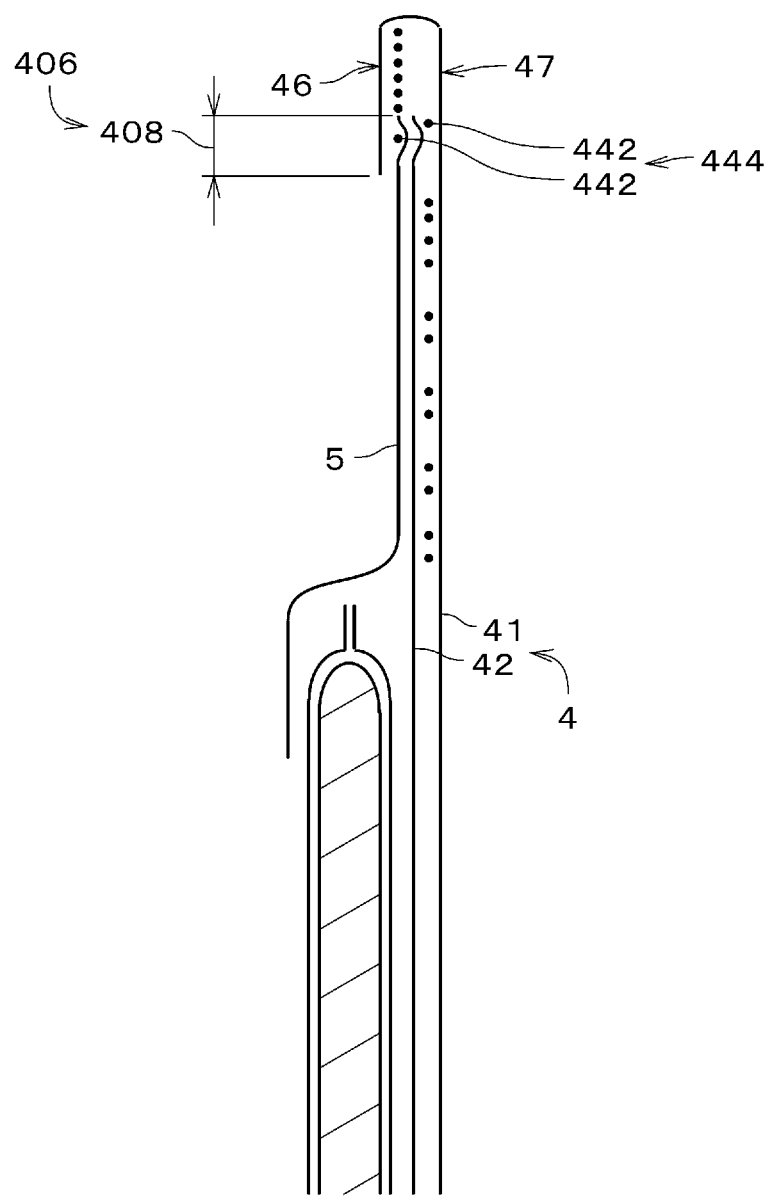

[Fig. 11]
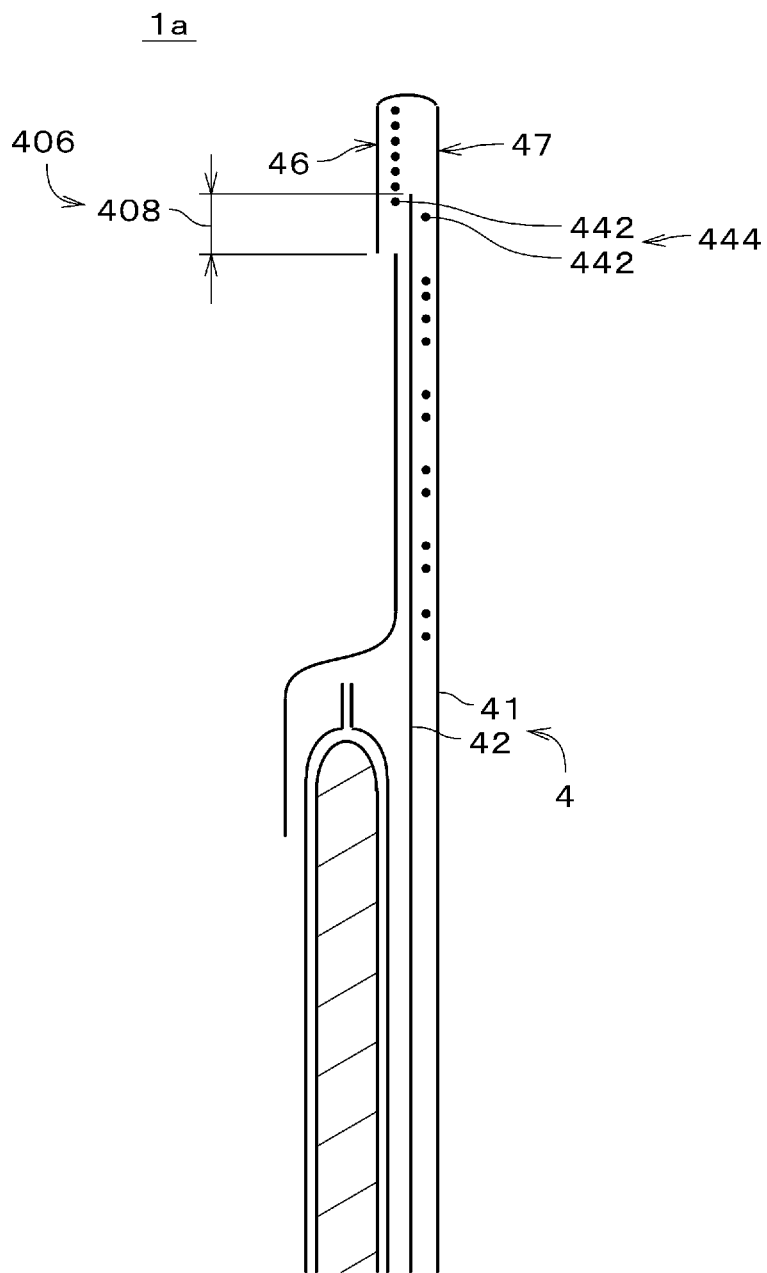

[Fig. 12]
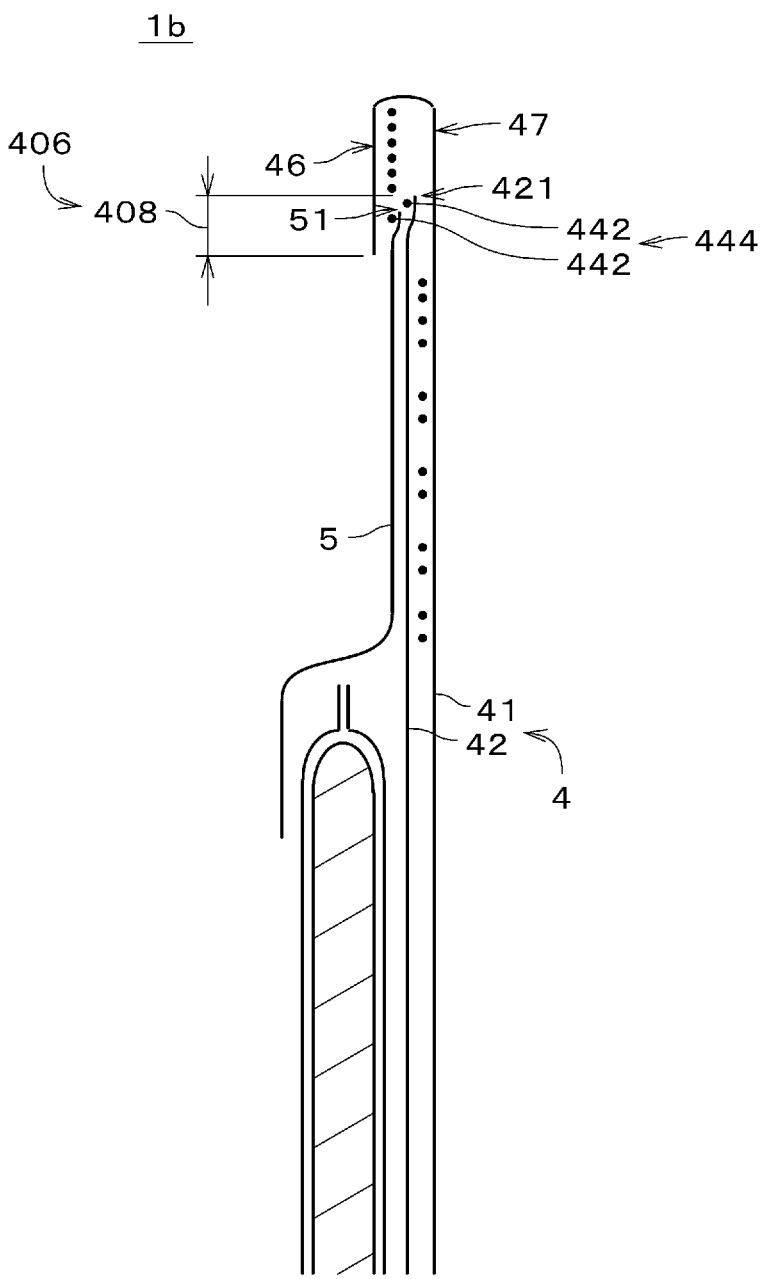

[Fig. 13]
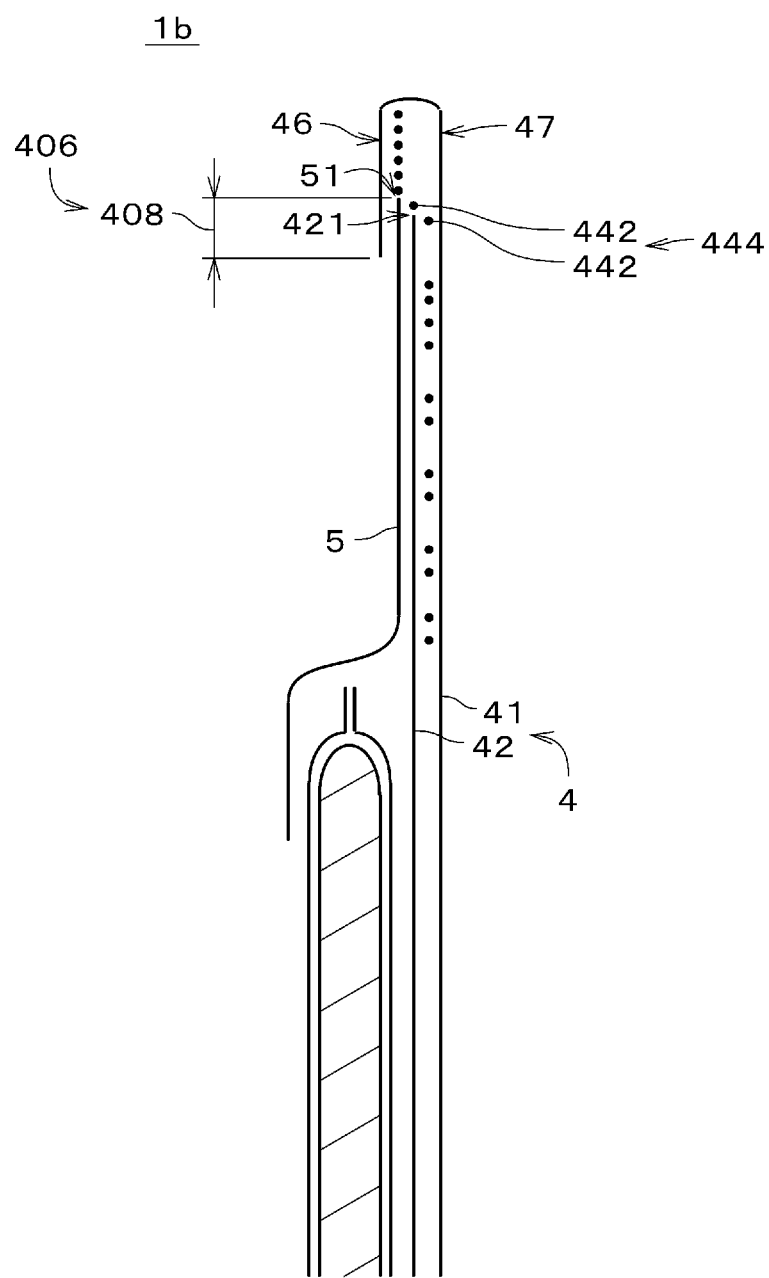

[Fig. 14]
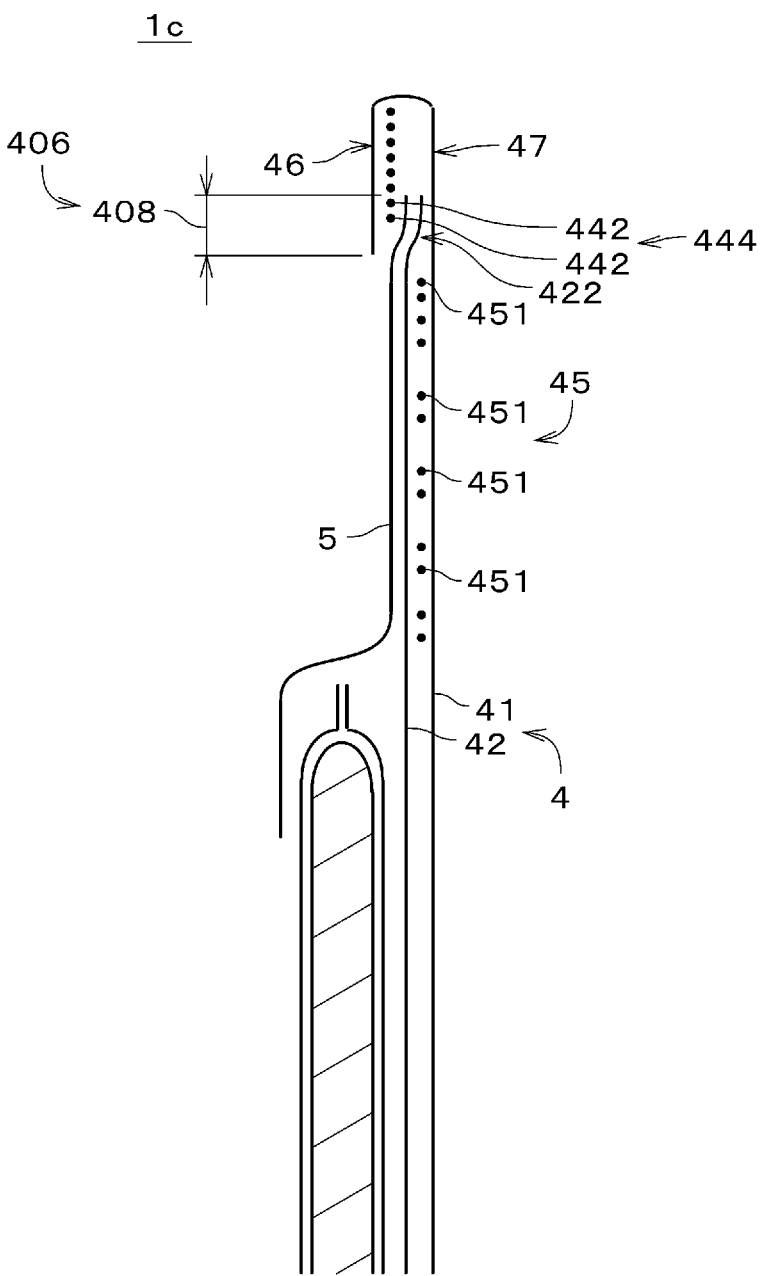

PANTS-TYPE ABSORBENT ARTICLE

TECHNICAL FIELD

The present invention relates to an absorbent article.

BACKGROUND ART

Pants-type disposal diapers having a waist opening at the top end and a pair of leg openings in the lower portion have conventionally been used as one type of absorbent article for receiving body waste discharged from a wearer. In pants-type disposal diapers, a waist elastic member along the edge of the waist opening is provided in front and rear parts located on the front and back sides of the wearer. Leg elastic members along the edges of the pair of leg openings are provided in a crotch part located between the front and rear parts. Furthermore, intermediate elastic members disposed between the waist elastic member and the leg elastic members in the vertical direction are provided in the front and rear parts.

In a pants-type disposal diaper disclosed in Japanese Patent Application Laid-Open No. 9-38133 (Document 1 ), a diaper main body includes an inner sheet and an outer sheet, and an elastic member for forming waist gathers and an elastic member for forming body gathers are joined in a stretched state between the inner sheet and the outer sheet. An absorbent is joined to the inner side of the diaper main body, and both longitudinal ends of the absorber are covered with an end-holding sheet in a region where the elastic member for forming body gathers is disposed. In the disposal diaper of Document 1 , in the region where the elastic member for forming body gathers is disposed, a two-layered region constituted by the inner sheet and the outer sheet is disposed on the upper side of the end-holding sheet so that dampness around the waist can easily escape to the outside.

In a pants-type disposal diaper disclosed in Japanese Patent Application Laid-Open No. 2006-247009 (Document 2 ), an elastic ribbon is attached to the opening around the waist. The elastic ribbon is formed by folding a nonwoven fabric in two to sandwich a stretchable elastic member. The elastic ribbon is joined to sandwich both longitudinal ends of a laminate of an absorbent main body and an exterior member in a unjoined portion of the end of the twofold nonwoven fabric.

When wearing a pants-type disposal diaper, the wearer usually inserts his/her legs into the leg openings and then pulls the disposal diaper up while grasping portions around the waist opening. In the disposal diaper of Document 1 , however, the elastic member for forming waist gathers is disposed in only the area where the outer sheet is folded, and no elastic member is disposed in the joining portion between the folded portion of the outer sheet and the inner sheet. Thus, the folded portion of the outer sheet and the inner sheet may be delaminated from each other or the area around the joining portion may be damaged when the disposal diaper is pulled up. In the disposal diaper of Document 2 , the elastic ribbon may become detached from the absorbent main body and the exterior member when the disposal diaper is pulled up.

SUMMARY OF INVENTION

The present invention is intended for an absorbent article, and it is an object of the present invention to improve breathability of an upper portion of a waist circumferential region and to reduce damage to an exterior sheet in the waist circumferential region.

A pants-type absorbent article according to the present invention includes an exterior sheet having a waist opening at an upper end and a pair of leg openings in a lower portion, and an absorber attached to an inner surface of the exterior sheet. The exterior sheet includes a front part, a rear part having side ends that are connected to side ends of the front part, a crotch part continuous with the front part and the rear part, a waist elastic member joined to the front part and the rear part in a waist circumferential region located along an edge of the waist opening, and configured to contract to form a waist opening gather, a leg elastic member joined to the crotch part along edges of the pair of leg openings, and configured to contract to form a pair of leg opening gathers, and an intermediate elastic member joined to the front part and the rear part in a region located between the waist elastic member and the leg elastic member in a vertical direction, and configured to contract to form an intermediate gather. The waist elastic member includes a first waist elastic member that, in a first waist circumferential region that is an upper portion of the waist circumferential region and is formed by laminating two sheet members, is joined between the two sheet members and generally parallel to the edge of the waist opening, and a second waist elastic member that, in a second waist circumferential region that is located below the first waist circumferential region in the waist circumferential region and is formed by laminating at least three sheet members, is joined between any of the at least three sheet members and generally parallel to the first waist elastic member. Among the at least three sheet members, one sheet member to which at least part of the second waist elastic member is directly joined has a bending resistance of 80 mm or less in a horizontal direction, when a test specimen having a width of 20 mm and a length of 150 mm is used in a 45 degree cantilever method. This absorbent article can improve breathability of the upper portion of the waist circumferential region and reduce damage to the exterior sheet in the waist circumferential region.

In a preferred embodiment of the present invention, a total of the bending resistance of the one sheet member in the horizontal direction and a binding resistance of the one sheet member in the vertical direction when the test specimen is used in the 45 degree cantilever method is 130 mm or less.

In another preferred embodiment of the present invention, the one sheet member has a tensile strength of 1.6 N/cm or more in the vertical direction.

In yet another preferred embodiment of the present invention, the second waist elastic member includes a plurality of elastic threads, and at least a portion of the plurality of elastic threads are disposed between an outermost sheet member and a sheet member that faces the outermost sheet member among the at least three sheet members in the second waist circumferential region.

More preferably, another portion of the plurality of elastic threads are disposed between two sheet members excluding the outermost sheet member among the at least three sheet members in the second waist circumferential region.

In yet another preferred embodiment of the present invention, the second waist elastic member is disposed between two sheet members excluding an outermost sheet member among the at least three sheet members in the second waist circumferential region, the outermost sheet member and a sheet member that faces the outermost sheet member are not joined in the second waist circumferential region, at least an upper end portion of the intermediate elastic member is disposed and joined between the outermost sheet member and the sheet member facing the outermost sheet member, in a lower portion of the waist circumferential region, and a distance in the vertical direction between a lower end of the second waist elastic member and an upper end of the intermediate elastic member is 30 mm or less.

In yet another preferred embodiment of the present invention, the at least three sheet members in the second waist circumferential region includes an outermost sheet member, an innermost sheet member, and two sheet members sandwiched between the outermost sheet member and the innermost sheet member and having upper ends located at different positions in the vertical direction. The second waist elastic member includes a plurality of elastic threads, a portion of the plurality of elastic threads being disposed between one of the outermost sheet member and the innermost sheet member and one of the two sheet members, and another portion of the plurality of elastic threads being disposed between the one of the outermost sheet member and the innermost sheet member and the other of the two sheet members.

These and other objects, features, aspects and advantages of the present invention will become more apparent from the following detailed description of the present invention when taken in conjunction with the accompanying drawings.

BRIEF DESCRIPTION OF DRAWINGS

FIG. 1 is a front view of a disposal diaper according to a first embodiment.

FIG. 2 is a rear view of the disposal diaper.

FIG. 3 is a plan view of the laid out disposal diaper.

FIG. 4 is a cross-sectional view of the disposal diaper.

FIG. 5 is a partial cross-sectional view of the disposal diaper.

FIG. 6 is a partial cross-sectional view of a disposal diaper according to a second embodiment.

FIG. 7 is a partial cross-sectional view of another disposal diaper.

FIG. 8 is a partial cross-sectional view of yet another disposal diaper.

FIG. 9 is a partial cross-sectional view of yet another disposal diaper.

FIG. 10 is a partial cross-sectional view of yet another disposal diaper.

FIG. 11 is a partial cross-sectional view of yet another disposal diaper.

FIG. 12 is a partial cross-sectional view of a disposal diaper according to a third embodiment.

FIG. 13 is a partial cross-sectional view of another disposal diaper.

FIG. 14 is a partial cross-sectional view of a disposal diaper according to a fourth embodiment.

DESCRIPTION OF EMBODIMENTS

FIGS. 1 and 2 are respectively a front view and a rear view of a disposal diaper 1 according to a first embodiment of the present invention (i.e., views of areas located on the front and back sides of a wearer). As illustrated in FIG. 1 and FIG. 2, the disposal diaper 1 is a pants-type absorbent article having a waist opening 11 at the upper end (i.e., end on the upper side in FIGS. 1 and 2) and a pair of leg openings 12 in the lower portion, and is configured to receive body waste discharged from the wearer.

FIG. 3 is a plan view of the laid out disposal diaper 1 viewed from the wearer side. The disposal diaper 1 includes an exterior sheet 4 having the waist opening 11 and the pair of leg openings 12 (see FIGS. 1 and 2) and a generally sheet-like absorber 20 that is attached to the inner surface of the exterior sheet 4 (i.e., surface on the wearer side) and is configured to absorb body waste discharged from the wearer. The exterior sheet 4 includes an exterior sheet main body 40, and leg elastic members 43, a waist elastic member 44 and intermediate elastic members 45 that are joined to the exterior-sheet main body 40.

In the disposal diaper 1, the upper area in FIG. 3 covers the front side (skin on the stomach side) of the wearer, and the lower area in FIG. 3 covers the back side (skin on the back side) of the wearer. In the following description, areas of the exterior sheet main body 40 that are located on the belly side and back side of the wearer are respectively referred to as a "front part 401" and a "rear part 403," and an area that is located between and continuous with the front part 401 and the rear part 403 and covers a groin part of the wearer is referred to as a "crotch part 402." In the disposal diaper 1, the exterior sheet 4 includes the front part 401, the crotch part 402, and the rear part 403. The absorber 20 extends from the front part 401 of the exterior sheet 4 to the rear part 403 via the crotch part 402.

In the manufacture of the disposal diaper 1, the exterior sheet 4 is folded at the crotch part 402 along with the absorber 20, and the inner surface of a strip area 404 located on both the left and right sides of the front part 401 and the inner surface of a strip area 405 located on both the left and right sides of the rear part 403 when the crotch part 402 is on the bottom side are joined to each other by heat sealing through the application of heat and pressure. The inner surfaces of the strip areas 404 are surfaces that are laterally continuous with both side ends of the inner surface of the front part 401, which is the surface that contacts the wearer, and are surfaces on the near side in FIG. 3. The inner surfaces of the strip areas 405 are surfaces that are laterally continuous with the both side ends of the inner surface of the rear part 403, which is the surface that contacts the wearer, and are surfaces on the near side in FIG. 3.

By joining the pair of strip areas 404 and the pair of strip areas 405 in this way, the side ends of the front part 401 and the side ends of the rear part 403 are connected as illustrated in FIGS. 1 and 2, forming the waist opening 11 at the upper ends of the front part 401 and the rear part 403. Also, the pair of leg openings 12 are respectively formed on the right and left sides of the crotch part 402 below the front part 401 and the rear part 403, and a pair of vertically extending strip projecting portions 13 are formed between the waist opening 11 and the leg openings 12. The strip projecting portions 13 are strip areas that each project laterally from a connecting line 400 between the front part 401 and the rear part 403.

FIG. 4 is cross-sectional view of the disposal diaper 1, taken along line Iv-Iv (i.e., at the crotch part 402) in FIG. 3. For convenience of illustration, constituent elements of the disposal diaper 1 are illustrated separately from each other in FIG. 4. As illustrated in FIGS. 3 and 4, the absorber 20 includes a generally sheet-like main body part 2 and a pair of side sheets 3 that are disposed one on either side portion of the main body part 2 (i.e., either side in the horizontal direction perpendicular to the vertical direction) and extends along approximately the entire longitudinal length of the main body part 2. The main body part 2 includes a top sheet 21, a back sheet 23, and an absorbent core 22 disposed between the top sheet 21 and the back sheet 23 as illustrated in FIG. 4. In order to facilitate understanding of the illustration, the contour of the absorbent core 22 of the absorber 20 is shown by the bold broken line in FIG. 3 (the same applies to FIGS. 1 and 2).

As illustrated in FIG. 3, the absorbent core 22 has a greater width at its opposite longitudinal sides than at its central portion in the longitudinal direction. In other words, the absorbent core 22 has a so-called hourglass shape. The back sheet 23 in FIG. 4 is joined to the exterior sheet 4 with a hot-melt adhesive or the like, and accordingly the absorber 20 is fixed to the exterior sheet 4.

As illustrated in FIG. 4, the pair of side sheets 3 each include a strip joining portion 33 and a side wall portion 34, the strip joining portion 33 being an area on one side of a folding line 39 that extends along the entire longitudinal length, and the side wall portion 34 being an area on the other side of the folding line 39. The pair of joining portions 33 are joined using a hot-melt adhesive to the upper side of the main body part 2 (i.e., wearer side) along approximately the entire longitudinal length in the vicinity of the lateral edges of the main body part 2. The pair of side wall portions 34 are areas that are continuous with the pair of joining portions 33 at the outer horizontal edges, i.e., the folding lines 39, of the joining portions 33 and extends along approximately the entire longitudinal length of the main body part 2 on the opposite side portions of the main body part 2.

The pair of side wall portions 34 are stacked on the joining portions 33 at the opposite longitudinal edges and are fixed to the joining portions 33 by, for example, heat seal bonding, ultrasonic bonding, or bonding with a hot-melt adhesive. Free edges of the side wall portions 34 are joined to side wall elastic members 35, and the side wall elastic members 35 are configured to contract to form gathers.

FIG. 5 is a partial cross-sectional view of the disposal diaper 1, taken along line V-V in FIG. 3. FIG. 5 shows the front side of the disposal diaper 1. The back-side structure of the disposal diaper 1 is the same as the front-side structure shown in FIG. 5. As illustrated in FIGS. 4 and 5, the exterior sheet main body 40 of the exterior sheet 4 includes a first exterior sheet 41 and a second exterior sheet 42 that is directly laminated onto the inner surface of the first exterior sheet 41 (i.e., wearer side) and joined thereto with a hot-melt adhesive or the like. The second exterior sheet 42 is joined to the inner surface of the first exterior sheet 41 up to its upper end 421.

As illustrated in FIG. 5, the exterior sheet main body 40 further includes an end sheet 5 that is directly laminated onto the inner surface of the second exterior sheet 42 and joined thereto with a hot-melt adhesive or the like. The end sheet 5 is disposed along approximately the entire width of the exterior sheet 4 in the horizontal direction of the disposal diaper 1 (i.e., lateral direction in FIG. 3) as illustrated in FIG. 3 and is fixed to the second exterior sheet 42 with the upper end portion of the absorber 20 sandwiched in between as illustrated in FIG. 5.

The upper end 421 of the second exterior sheet 42 is at approximately the same position as an upper end 51 of the end sheet 5 in the vertical direction and is spaced below an edge 111 of the waist opening 11, which is the upper end of the first exterior sheet 41. The upper end 421 of the second exterior sheet 42 and the upper end 51 of the end sheet 5 are located above the upper end 25 of the absorber 20.

The top sheet 21 of the absorber 20 illustrated in FIG. 4 is a liquid-permeable sheet material that quickly catches moisture in body waste discharged from the wearer and moves the moisture to the absorbent core 22. Examples of the top sheet 21 include liquid-permeable nonwoven fabrics (e.g., point-bonded nonwoven fabrics, air-through nonwoven fabrics, and spun-bonded nonwoven fabrics) formed from hydrophobic fibers having a surface that has undergone hydrophilic treatment using a surfactant (e.g., polypropylene, polyethylene, polyester, polyamide or nylon). Alternatively, the top sheet 21 may be a nonwoven fabric (e.g., a spunlace nonwoven fabric) formed from hydrophilic fibers such as cellulose, rayon, or cotton.

The absorbent core 22 is formed by mixing a super-absorbent material such as a granular super-absorbent polymer (SAP) or super-absorbent fibers with hydrophilic fibers such as comminuted pulp fibers or cellulose fibers and then wrapping that mixture in tissue paper, a liquid-permeable nonwoven fabric, or the like. The absorbent core 22 can absorb and quickly traps moisture permeating through the top sheet 21. The tissue paper, the liquid-permeable nonwoven fabric, or the like that is wrapped around the hydrophilic fibers is joined to the hydrophilic fibers and a water-absorbent material with a hot-melt adhesive, thus preventing deformation of the hydrophilic fibers and detachment of the water-absorbent material (in particular, detachment after water absorption). In the present embodiment, the absorbent core 22 includes pulp fibers and an SAP.

Examples of the back sheet 23 include water-repellent or liquid impermeable nonwoven fabrics formed from hydrophobic fibers (e.g., spun-bonded nonwoven fabrics, melt-blown nonwoven fabrics, and spun-melt-spun (SMS) nonwoven fabrics) and water-repellent or liquid impermeable plastic films. The back sheet 23 prevents moisture or the like in body waste that has reached the back sheet 23 from leaking outside the main body part 2. When the back sheet 23 is formed from a plastic film, it is preferable to use a plastic film having vapor permeability (breathability) from the viewpoint of preventing the disposal diaper 1 from getting sweaty and improving comfort for the wearer.

Examples of the sheet main body of the side sheet 3 include water-repellent or liquid impermeable nonwoven fabrics formed from hydrophobic fibers (e.g., spun-bonded nonwoven fabrics, melt-blown nonwoven fabrics, and SMS nonwoven fabrics). Examples of the side wall elastic members 35 include polyurethane threads, strip polyurethane films, and filiform or strip natural rubber. In the present embodiment, polyurethane threads are used as the side wall elastic members 35.

Similarly to the back sheet 23, the first and second exterior sheets 41 and 42 of the exterior sheet main body 40 and the end sheet 5 illustrated in FIG. 5 may be a water-repellent or liquid impermeable nonwoven fabric formed from hydrophobic fibers (e.g., a spun-bonded nonwoven fabric, a melt-blown nonwoven fabric, or an SMS nonwoven fabric), a plastic film, or a laminated sheet of such a nonwoven fabric and a plastic film. It is preferable for the plastic film to have vapor permeability (breathability). Alternatively, similarly to the top sheet 21, the first exterior sheet 41, the second exterior sheet 42, and the end sheet 5 may be a nonwoven fabric formed from hydrophilic fibers or a liquid-permeable nonwoven fabric formed from hydrophobic fibers that have undergone hydrophilic treatment.

The first exterior sheet 41 of the exterior sheet 4 includes a folded portion 46 that is folded toward the wearer at the edge 111 of the waist opening 11. A lower end of the folded portion 46 is located below the upper end 421 of the second exterior sheet 42 and the upper end 51 of the end sheet 5 and above the upper end 25 of the absorber 20. An upper end portion 422 of the second exterior sheet 42 and an upper end portion 52 of the end sheet 5 are sandwiched between the folded portion 46 and an opposing portion 47 of the first exterior sheet 41 that faces the folded portion 46. The folded portion 46 is joined to the opposing portion 47 and the upper end portion of the end sheet 5.

In the following description, a strip region of the exterior sheet 4 that ranges from the edge 111 of the waist opening 11 to the lower end 461 of the folded portion 46 is referred to as a "waist circumferential region 406." The waist circumferential region 406 is disposed along the edge 111 of the waist opening 11. In the present embodiment, the waist circumferential region 406 has a vertical width of 50 mm or less. As described above, the lower end 461 of the folded portion 46 is located above the upper end 25 of the absorber 20, and thus the waist circumferential region 406 is also located above the upper end 25 of the absorber 20.

Also, in the following description, a strip region that is an upper portion of the waist circumferential region 406 and is formed by laminating two sheet members, namely the folded portion 46 and the opposing portion 47, is referred to as a "first waist circumferential region 407." The portion of the waist circumferential region 406 other than the first waist circumferential region 407, i.e., a strip region located below and continuous with the first waist circumferential region 407 in the waist circumferential region 406 is referred to as a "second waist circumferential region 408." The second waist circumferential region 408 is formed by laminating four sheet members, namely, the folded portion 46 and opposing portion 47 of the first exterior sheet 41, the second exterior sheet 42, and the end sheet 5. The first waist circumferential region 407 has a vertical width at least half the vertical width of the waist circumferential region 406. In the present embodiment, the vertical width of the first waist circumferential region 407 is greater than that of the second waist circumferential region 408.

In the waist circumferential region 406, the waist elastic member 44 is disposed along the edge 111 of the waist opening 11 and extends in the horizontal direction to be joined to the front part 401 and the rear part 403. In the disposal diaper 1, the exterior sheet main body 40 contracts by contraction of the waist elastic member 44, forming waist opening gathers that contact the wearer.

As illustrated in FIG. 5, the waist elastic member 44 includes a first waist elastic member 443 and a second waist elastic member 444. The first waist elastic member 443 is disposed between the folded portion 46 and the opposing portion 47 and generally parallel to the edge 111 of the waist opening 11 in the first waist circumferential region 407, and is directly joined to the folded portion 46 and the opposing portion 47. The second waist elastic member 444 is disposed between two adjacent sheet members among the folded portion 46 and opposing portion 47 of the first exterior sheet 41, the second exterior sheet 42, and the end sheet 5 and generally parallel to the first waist elastic member 443 in the second waist circumferential region 408, and is directly joined to the two sheet members.

In the present embodiment, the first waist elastic member 443 includes six first elastic threads 441, and the second waist elastic member 444 includes two second elastic threads 442. The six first elastic threads 441 and the two second elastic threads 442 are arranged at an approximately equal pitch in the vertical direction and each extend generally parallel to the edge 111 of the waist opening 11. The two second elastic threads 442 are disposed and joined between the folded portion 46 and the end sheet 5, the folded portion 46 being the innermost sheet member (closest to the wearer side) among the four sheet members of the second waist circumferential region 408, and the end sheet 5 being a sheet member that faces the innermost sheet member.

As illustrated in FIGS. 1 and 2, the leg elastic members 43 are disposed along edges 121 of the pair of leg openings 12 and are joined between the first and second exterior sheets 41 and 42 of the exterior sheet 4 (see FIG. 4). Focusing on each of the leg elastic members 43, opposite upper ends are joined to the front part 401 and the rear part 403, and a central portion between the opposite upper ends is joined to the crotch part 402 of the exterior sheet main body 40. The leg elastic members 43 each include a plurality of leg elastic threads 431. In the disposal diaper 1, the exterior sheet main body 40 contracts by contraction of the leg elastic members 43, forming leg gathers that contact the circumference of the legs of the wearer.

The intermediate elastic members 45 are disposed in regions between the waist elastic member 44 and the upper ends of the leg elastic members 43 in the vertical direction and extend in the horizontal direction to be joined to the front part 401 and the rear part 403. As illustrated in FIG. 5, the intermediate elastic members 45 are disposed and joined between the first exterior sheet 41 and the second exterior sheet 42. The intermediate elastic members 45 each include a plurality of (in the present embodiment, 12 ) intermediate elastic threads 451 that are arranged in the vertical direction and extend generally parallel to the first and second elastic threads 441 and 442 of the waist elastic member 44. In the disposal diaper 1, the exterior sheet main body 40 contracts by contraction of the intermediate elastic members 45, forming intermediate gathers that contact the hypogastric and hip regions of the wearer.

In the present embodiment, the first elastic threads 441 and second elastic threads 442 of waist elastic member 44, the leg elastic threads 431 of the leg elastic member 43 (see FIGS. 1 and 2), and the intermediate elastic threads 451 of the intermediate elastic members 45 are polyurethane threads. These elastic threads 441, 442, 431, and 451 may have coefficients of elasticity and degrees of fineness that are different from or the same as each other.

In the disposal diaper 1, the folded portion 46 of the first exterior sheet 41 and the end sheet 5, which are two sheet members directly joined to the second waist elastic member 444 among the four sheet members forming the second waist circumferential region 408, each have a horizontal bending resistance of 80 mm or less, the horizontal bending resistance being a bending resistance in the horizontal direction. A method and conditions for measuring the bending resistance will be described later. Preferably, the folded portion 46 and the end sheet 5 each have a horizontal bending resistance of 70 mm or less, and more preferably, 65 mm or less. Also, a total (hereinafter, referred to as a "total bending resistance") of the horizontal bending resistance of the folded portion 46 and a vertical bending resistance thereof, which is a bending resistance in the vertical direction, is preferably 130 mm or less. A total bending resistance of the end sheet 5 is also preferably 130 mm or less. More preferably, the folded portion 46 and the end sheet 5 each have a total bending resistance of 110 mm or less, and yet more preferably, 95 mm or less.

The bending resistance of each sheet member is measured using a cantilever testing machine in a testing method (45 degree cantilever method) according to JIS-L-1086. A test specimen to be used is obtained by cutting a sheet member to be measured into a generally rectangular shape having a length of 150 mm in a direction in which the bending resistance is measured (i.e., horizontal direction when the horizontal bending resistance is measured, or vertical direction when the vertical bending resistance is measured) and a width of 20 mm in the direction perpendicular to the direction in which the bending resistance is measured.

In the disposal diaper 1, the folded portion 46 and the end sheet 5 each preferably have a vertical tensile strength of 1.6 N/cm or more. More preferably, the vertical tensile strength is 2.0 N/cm or more, and yet more preferably, 2.6 N/cm or more.

The tensile strength of each sheet member is measured using a "TENSILON (model type: RTG-1210)" manufactured by A&D Company, Limited as a measuring machine. First, a sheet member to be measured is cut to prepare a generally rectangular test specimen having a length of 250 mm in the vertical direction, which is a direction in which the tensile strength is measured, and a width of 50 mm in the horizontal direction perpendicular to the direction in which the tensile strength is measured. Then, opposite vertical ends of the test specimen (i.e., areas in the vicinity of the opposite short sides of the test specimen) are grasped by a clamp portion of the measuring machine. Next, the test specimen is pulled in the vertical direction by the measuring machine and loads are measured until the test specimen is damaged, thereby acquiring a maximum load that can be applied to the test specimen. This measurement of a maximum load is conducted three times, and an average value of the maximum loads is acquired as a tensile strength of the test specimen.

As described above, in the disposal diaper 1, the first waist circumferential region 407 is formed by laminating the two sheet members, namely, the folded portion 46 and opposing portion 47 of the first exterior sheet 41. It is thus possible to improve breathability of the first waist circumferential region 407 and to reduce stuffiness.

In the disposal diaper 1, it is sufficient that at least one of the folded portion 46 and the end sheet 5 (i.e., one sheet member that is directly joined to the second waist elastic member 444) has a horizontal bending resistance of 80 mm or less in the above-described measurement environment. This reduces the horizontal bending resistance of the second waist circumferential region 408 and accordingly improves flexibility thereof, thus allowing the second waist circumferential region 408 to easily contract by contraction of the second waist elastic member 444. The thickness and strength of the second waist circumferential region 408 increase accordingly, which makes it possible to reduce damage to the exterior sheet 4 in the waist circumferential region 406 (e.g., detachment of the folded portion 46 from the end sheet 5 or detachment of the opposing portion 47 from the second exterior sheet 42), which can be caused by, for example, areas in the vicinity of the waist opening 11 being grasped and pulled up when the disposal diaper 1 is worn.

Furthermore, the above-described one sheet member, which has a total bending resistance of 130 mm or less in the above-described measurement environment, can further reduce damage to the exterior sheet 4 in the waist circumferential region 406 because the second waist circumferential region 408 can more easily contract. In addition, the above-described one sheet member, which has a vertical tensile strength of 1.6 N/cm or more, can further reduce the occurrence of the waist circumferential region 406 of the disposal diaper 1 being damaged when pulled in the vertical direction.

In the disposal diaper 1, as described above, the folded portion 46 and the end sheet 5 both have a horizontal bending resistance of 80 mm or less, i.e., not only the above-described sheet member but another sheet member that is directly joined to the second waist elastic member 444 have a horizontal bending resistance of 80 mm or less. This improves flexibility of the second waist circumferential region 408 and allows the second waist circumferential region 408 to more easily contract. The thickness and strength of the second waist circumferential region 408 increase accordingly, which makes it possible to further reduce damage to the exterior sheet 4 in the waist circumferential region 406.

The other sheet member, which has a total bending resistance of 130 mm or less, can further reduce damage to the exterior sheet 4 in the waist circumferential region 406 because the second waist circumferential region 408 can more easily contract. In addition, the other sheet member, which has a vertical tensile strength of 1.6 N/cm or more, can further reduce the occurrence of the waist circumferential region 406 of the disposal diaper 1 being damaged when pulled in the vertical direction.

In the disposal diaper 1, as described above, the waist circumferential region 406 is located above the upper end 25 of the absorber 20. This avoids a situation in which the contraction of the second waist circumferential region 408 is interfered with by the absorber 20, and allows the second waist circumferential region 408 to easily contract, thus making it possible to further reduce damage to the exterior sheet 4 in the waist circumferential region 406.

In the disposal diaper 1, the folded portion 46 is formed by folding the first exterior sheet 41 of the exterior sheet 4 at the edge 111 of the waist opening 11, and the waist elastic member 44 is disposed and joined between the folded portion 46 and the opposing portion 47. Having such a fold of a continuous sheet member at the edge 111 of the waist opening 11 and at the upper ends of the pair of strip projecting portions 13 (see FIG. 1) improves the texture of the edge 111 of the waist opening 11 and the strip projecting portions 13 as compared with the case where sheet members have cut edges. Furthermore, including the lower end portion 462 of the folded portion 46 in the four sheet members of the second waist circumferential region 408 facilitates the formation of the second waist circumferential region 408. Also, the first waist circumferential region 407, which is formed of the two sheet members and has a vertical width at least half that of the waist circumferential region 406, can further improve breathability of the waist circumferential region 406.

As described above, the two second elastic threads 442 of the second waist elastic member 444 are disposed and joined between the innermost sheet member (folded portion 46) and the sheet member (end sheet 5) that faces the innermost sheet member among the four sheet members of the second waist circumferential region 408. By directly joining the second elastic threads 442 to the folded portion 46 in this way, a force that is applied to the folded portion 46 when a vertical force is applied to a portion of the waist circumferential region 406 can be dispersed in the horizontal direction by the second elastic threads 442. In this way, the second elastic thread 442 provides resistance to a vertical force. This makes it possible to suppress detachment of the folded portion 46 from the end sheet 5, the folded portion 46 being the innermost sheet member that is relatively easily damaged in the second waist circumferential region 408, and to further reduce damage to the exterior sheet 4 in the waist circumferential region 406.

In the disposal diaper 1, the number of first elastic threads 441 included in the first waist elastic member 443 and the number of second elastic threads 442 included in the second waist elastic member 444 may be appropriately changed. The second waist circumferential region 408 does not necessarily have to be formed of four sheet members, and it is sufficient for the second waist circumferential region 408 to be formed by lamination of at least three sheet members. Regarding the number of first elastic threads 441 and the number of second elastic threads 442, the same applies to the second to fourth embodiments, which will be described later. Regarding the number of layers of the second waist circumferential region 408, the same applies to the second and fourth embodiments.

In the disposal diaper 1, at least one sheet member among the at least three sheet members forming the second waist circumferential region 408 has a horizontal bending resistance of 80 mm or less. When the second waist elastic member 444 includes a plurality of second elastic threads 442, at least a portion of the second elastic threads 442 is directly joined to the aforementioned sheet member having a horizontal bending resistance of 80 mm or less. This allows a force applied to that sheet member to be dispersed in the horizontal direction by the second elastic threads 442, thus making it possible to reduce damage to the exterior sheet 4 in the waist circumferential region 406.

Preferably, another sheet member that is directly joined to the aforementioned portion of the second elastic threads 442 has a horizontal bending resistance of 80 mm or less. This makes it possible to further reduce damage to the exterior sheet 4 in the waist circumferential region 406. More preferably, at least a portion of the second elastic threads 442 is disposed and joined between the innermost sheet member (folded portion 46) and the sheet member (end sheet 5) that faces the innermost sheet member, among the four sheet members of the second waist circumferential region 408. By directly joining the second elastic threads 442 to the folded portion 46, which is the innermost sheet member that is relatively easily damaged, it is possible to further reduce damage to the exterior sheet 4 in the waist circumferential region 406.

Next, a disposal diaper according to a second embodiment of the present invention will be described. FIG. 6 is a partial cross-sectional view of the front side of a disposal diaper 1a according to the second embodiment. The back-side structure of the disposal diaper 1a is similar to the structure illustrated in FIG. 6. The disposal diaper 1a has the same structure as that of the disposal diaper 1 illustrated in FIGS. 1 to 5, with the exception that different sheet members are directly joined to the second waist elastic member 444 in the second waist circumferential region 408. In the following description, corresponding constituent elements are denoted by the same reference numerals.

In the disposal diaper 1a illustrated in FIG. 6, the second waist elastic member 444 includes two second elastic threads 442. The two sheet elastic threads 442 are disposed and joined between the opposing portion 47 of the first exterior sheet 41 and the second exterior sheet 42, the opposing portion 47 being the outermost sheet member among the four sheet members (folded portion 46, end sheet 5, second exterior sheet 42, and opposing portion 47) of the second waist circumferential region 408, and the second exterior sheet 42 being the sheet member that faces the opposing portion 47. By directly joining the second elastic threads 442 to the opposing portion 47, the second elastic threads 442 provide resistance to the force applied to the opposing portion 47 when a vertical force is applied to the waist circumferential region 406. It is thus possible to suppress detachment of the opposing portion 47 from the second exterior sheet 42, the opposing portion 47 being the outermost sheet member that is relatively easily damaged in the second waist circumferential region 408, and to accordingly reduce damage to the exterior sheet 4 in the waist circumferential region 406.

Alternatively, the disposal diaper 1a may have a structure in which one of the two second elastic threads 442 is disposed between the opposing portion 47 of the first exterior sheet 41 and the second exterior sheet 42, and as illustrated in FIGS. 7 to 10, the other second elastic thread 442 is disposed between any of the sheet members of the second waist circumferential region 408 excluding the opposing portion 47, which is the outermost sheet member. In FIG. 7, the upper second elastic thread 442 is disposed and joined between the second exterior sheet 42 and the end sheet 5, and in FIG. 8, the lower second elastic thread 442 is disposed and joined between the second exterior sheet 42 and the end sheet 5. It is thus possible to suppress detachment of the second exterior sheet 42 from the end sheet 5 when a vertical force is applied to the waist circumferential region 406 and to accordingly reduce damage to the exterior sheet 4 in the waist circumferential region 406.

In FIG. 9, the upper second elastic thread 442 is disposed and joined between the end sheet 5 and the folded portion 46, which is the innermost layer, and in FIG. 10, the lower second elastic thread 442 is disposed and joined between the end sheet 5 and the folded portion 46, which is the innermost layer. It is thus possible to suppress detachment of the folded portion 46 from the end sheet 5 when a vertical force is applied to the waist circumferential region 406 and to accordingly reduce damage to the exterior sheet 4 in the waist circumferential region 406.

As described above, the number of second elastic threads 442 and the number of layers in the second waist circumferential region 408 may be appropriately changed. For example, as illustrated in FIG. 11, the second waist circumferential region 408 may have a three-layered structure in which the second exterior sheet 42 is sandwiched between the folded portion 46 of the first exterior sheet 41 and the opposing portion 47 thereof. In FIG. 11, the lower second elastic thread 442 is disposed between the opposing portion 47 and the second exterior sheet 42, and the upper second elastic thread 442 is disposed and joined between the second exterior sheet 42 and the folded portion 46.

As described above, in the disposal diaper 1a illustrated in FIGS. 6 to 11, at least a portion of a plurality of second elastic threads 442 of the second waist elastic member 444 are disposed between the outermost sheet layer and the sheet member that faces the outermost sheet member among the three or more sheet members forming the second waist circumferential region 408. It is thus possible to suppress detachment of the outermost sheet member, which is relatively easily damaged in the second waist circumferential region 408 and to accordingly reduce damage to the exterior sheet 4 in the waist circumferential region 406. In addition, another portion of the second elastic threads 442 may be disposed between two sheet members excluding the outermost sheet member, among the three or more sheet members of the second waist circumferential region 408. It is thus possible to suppress detachment of these two sheet members and to accordingly further reduce damage to the exterior sheet 4 in the waist circumferential region 406.

Next, a disposal diaper according to a third embodiment of the present invention will be described. FIG. 12 is a partial cross-sectional view of the front side of a disposal diaper 1b according to the third embodiment. The back-side structure of the disposal diaper 1b is similar to the structure illustrated in FIG. 12. The disposal diaper 1b differs from the disposal diaper 1 in that the upper end 421 of the second exterior sheet 42 and the upper end 51 of the end sheet 5 are located at different vertical positions and that different sheet members are directly joined to the second waist elastic member 444 in the second waist circumferential region 408. The other constituent elements of the disposal diaper 1b are similar to those of the disposal diaper 1 illustrated in FIGS. 1 to 5, and corresponding constituent elements are denoted by the same reference numerals in the following description.

In the disposal diaper 1b illustrated in FIG. 12, the upper end 421 of the second exterior sheet 42 is located above the upper end 51 of the end sheet 5 (e.g., located closer to the waist opening 11). Among the two second elastic threads 442 of the second waist elastic member 444, the upper second elastic thread 442 is disposed and joined between the folded portion 46 of the first exterior sheet 41 and the second exterior sheet 42, and the lower second elastic thread 442 is disposed and joined between the folded portion 46 and the end sheet 5. It is thus possible to suppress detachment of the end sheet 5 and the second exterior sheet 42 from the folded portion 46 and to accordingly reduce damage to the exterior sheet 4 in the waist circumferential region 406.

Alternatively, the disposal diaper 1b may have a structure as illustrated in FIG. 13 in which the upper end 51 of the end sheet 5 is located above the upper end 421 of the second exterior sheet 42, the upper second elastic thread 442 of the second waist elastic member 444 is disposed between the end sheet 5 and the opposing portion 47, and the lower second elastic thread 442 is disposed between the second exterior sheet 42 and the opposing portion 47 of the first exterior sheet 41. It is thus possible to suppress detachment of the end sheet 5 and the second exterior sheet 42 from the opposing portion 47 and to accordingly further reduce damage to the exterior sheet 4 in the waist circumferential region 406.

As described above, in the disposal diaper 1b illustrated in FIGS. 12 and 13, a portion of a plurality of second elastic threads 442 of the second waist elastic member 444 is disposed between one of the folded portion 46 being the innermost sheet member and the opposing portion 47 being the outermost sheet member, and one of the end sheet 5 and the second exterior sheet 42 that are disposed between the folded portion 46 and the opposing portion 47. Also, another portion of the second elastic threads 442 is disposed between the aforementioned one of the folded portion 46 and the opposing portion 47 and the other of the end sheet 5 and the second exterior sheet 42. It is thus possible to suppress detachment of the end sheet 5 and the second exterior sheet 42 from the area between the folded portion 46 and the opposing portion 47 and to accordingly further reduce damage to the exterior sheet 4 in the waist circumferential region 406. Alternatively, the disposal diaper 1b may also have a configuration in which, for example, the second waist circumferential region 408 may be formed of five or more sheet members by providing other sheet members between the end sheet 5 and the second exterior sheet 42.

Next, a disposal diaper according to a fourth embodiment of the present invention will be described. FIG. 14 is a partial cross-sectional view of the front side of a disposal diaper 1c according to the fourth embodiment. The backside structure of the disposal diaper 1c is similar to the structure illustrated in FIG. 14. In the disposal diaper 1c, the upper end portion 422 of the second exterior sheet 42 and the inner surface of the first exterior sheet 41 are not joined throughout the entire second waist circumferential region 408. The other constituent elements of the disposal diaper 1c are similar to those of the disposal diaper 1 illustrated in FIGS. 1 to 5, and corresponding constituent elements are denoted by the same reference numerals in the following description.

As illustrated in FIG. 14, the two second elastic threads 442 of the second waist elastic member 444 are disposed and joined between the folded portion 46 and the end sheet 5. In the disposal diaper 1c, the number of second elastic threads 442 may be one or three or more. The second elastic threads 442 may be disposed and joined between the end sheet 5 and the second exterior sheet 42. The second elastic threads 442 may be disposed and joined between each of the folded portion 46, the end sheet 5, and the second exterior sheet 42. In other words, the second waist elastic member 444 is disposed between two sheet members excluding the opposing portion 47, which is the outermost sheet member, among the at least three sheet members of the second waist circumferential region 408.

Below the waist circumferential region 406, at least an upper end portion of each of the intermediate elastic members 45, i.e., at least one intermediate elastic thread 451 that is disposed in the upper end portion among a plurality of intermediate elastic threads 451 of the intermediate elastic member 45, is disposed and joined between the first exterior sheet 41, which is the outermost sheet member, and the second exterior sheet 42, which is the sheet member that faces the first exterior sheet 41. In the present embodiment, all of the intermediate elastic threads 451 of the intermediate elastic members 45 are disposed and joined between the first exterior sheet 41 and the second exterior sheet 42. Note that in the disposal diaper 1c, the distance in the vertical direction between the lower end of the second waist elastic member 444 and the upper ends of the intermediate elastic members 45, i.e., between the second elastic thread 442 located at the lowermost position and the intermediate elastic thread 451 located at the uppermost position, is 30 mm or less.

The disposal diaper 1c can improve breathability of the second waist circumferential region 408 and can improve the feel of the second waist circumferential region 408 because the first exterior sheet 41 and the second exterior sheet 42 are not joined in the second waist circumferential region 408. Furthermore, by joining the intermediate elastic members 45 to the first exterior sheet 41 at a position below and in the vicinity of a region where the first exterior sheet 41 and the second exterior sheet 42 are not joined (i.e., a position within a distance of 30 nm), it is possible to reduce damage to the first exterior sheet 41 in the second waist circumferential region 408 or the like and to accordingly further reduce damage to the exterior sheet 4 in the waist circumferential region 406.

Various modifications can be made to the above-described disposal diapers.

For example, the first exterior sheet 41 does not necessarily have to include the folded portion 46, and a sheet member that has a similar shape to the folded portion 46 and is not continuous with the first exterior sheet 41 may be joined at the same position as the folded portion 46, with the upper end of the sheet member being at approximately the same position as the upper end of the first exterior sheet 41. In this case, the waist circumferential region 406 ranges from the upper ends of that sheet member and the first exterior sheet 41 to the lower end of that sheet member. The vertical width of the waist circumferential region 406 and the ratio of the vertical width of the first waist circumferential region 407 to the vertical width of the waist circumferential region 406 may be appropriately changed.

The leg elastic member 43, the waist elastic member 44, and the intermediate elastic members 45 may, for example, be strip polyurethane films or filiform or strip natural rubber, similarly to the side wall elastic members 35 of the side sheets 3.

The above-described structure of the disposal diaper 1 may be used for pants-type absorbent articles other than disposal diapers.

The configurations of the above-described embodiments and variations may be appropriately combined as long as there are no mutual inconsistencies.

While the invention has been shown and described in detail, the foregoing description is in all aspects illustrative and not restrictive. It is therefore understood that numerous modifications and variations can be devised without departing from the scope of the invention.

REFERENCE SIGNS LIST 1, 1a to 1c Disposal diaper
4 Exterior sheet
5 End sheet
11 Waist opening
12 Leg opening
20 Absorber
25 Upper end (of absorber)
41 First exterior sheet
42 Second exterior sheet
43 Leg elastic member
44 Waist elastic member
45 Intermediate elastic member
46 Folded portion
47 Opposing portion
51 Upper end (of end sheet)
111 Edge (of waist opening)
121 Edge (of leg opening)
401 Front part
402 Crotch part
403 Rear part
406 Waist circumferential region
407 First waist circumferential region
408 Second waist circumferential region
421 Upper end (of second exterior sheet)
442 Second elastic thread
443 First waist elastic member
444 Second waist elastic member
462 Lower end portion (of folded portion)

The invention claimed is:

1. A pants-type absorbent article comprising:
an exterior sheet having a waist opening at an upper end and a pair of leg openings in a lower portion; and
an absorber attached to an inner surface of said exterior sheet, wherein said exterior sheet includes:
a front part;
a rear part having side ends that are connected to side ends of said front part;
a crotch part continuous with said front part and said rear part;
a waist elastic member joined to said front part and said rear part in a waist circumferential region located along an edge of said waist opening, and configured to contract to form a waist opening gather;
a leg elastic member joined to said crotch part along edges of said pair of leg openings, and configured to contract to form a pair of leg opening gathers; and
an intermediate elastic member joined to said front part and said rear part in a region located between said waist elastic member and said leg elastic member in a vertical direction, and configured to contract to form an intermediate gather,
said waist elastic member includes:
a first waist elastic member that, in a first waist circumferential region that is an upper portion of said waist circumferential region and comprises two sheet members, is joined between said two sheet members and generally parallel to said edge of said waist opening; and
a second waist elastic member that, in a second waist circumferential region that is located below said first waist circumferential region in said waist circumferential region and comprises at least three sheet members, is joined between any of said at least three sheet members and generally parallel to said first waist elastic member, and
among said at least three sheet members, one sheet member to which at least part of said second waist elastic member is directly joined has a bending resistance of 80 mm or less in a horizontal direction, when a test specimen having a width of 20 mm and a length of 150 mm is used in a 45 degree cantilever method.

2. The absorbent article according to claim 1, wherein a total of the bending resistance of said one sheet member in said horizontal direction and a binding resistance of said one sheet member in said vertical direction when said test specimen is used in said 45 degree cantilever method is 130 mm or less.

3. The absorbent article according to claim 2, wherein another sheet member to which said at least part of said second waist elastic member is directly joined also has a bending resistance of 80 mm or less in said horizontal direction when said test specimen is used in said 45 degree cantilever method.

4. The absorbent article according to claim 3, wherein a total of the bending resistance of said other sheet member in said horizontal direction and a bending resistance of said other sheet member in said vertical direction when said test specimen is used in said 45 degree cantilever method is 130 mm or less.

5. The absorbent article according to claim 1, wherein another sheet member to which said at least part of said second waist elastic member is directly joined also has a bending resistance of 80 mm or less in said horizontal direction when said test specimen is used in said 45 degree cantilever method.

6. The absorbent article according to claim 5, wherein a total of the bending resistance of said other sheet member in said horizontal direction and a bending resistance of said other sheet member in said vertical direction when said test specimen is used in said 45 degree cantilever method is 130 mm or less.

7. The absorbent article according to claim 1, wherein said one sheet member has a tensile strength of 1.6 N/cm or more in said vertical direction.

8. The absorbent article according to claim 7, wherein another sheet member to which said at least part of said second waist elastic member is directly joined has a tensile strength of 1.6 N/cm or more in said vertical direction.

9. The absorbent article according to claim 1, wherein said waist circumferential region is located above an upper end of said absorber.

10. The absorbent article according to claim 1, wherein said waist circumferential region has a width of 50 mm or less in said vertical direction.

11. The absorbent article according to claim 1, wherein
said exterior sheet includes a folded portion that is folded toward a wearer at said edge of said waist opening, and
said first waist elastic member is joined between said folded portion and a portion of said exterior sheet that faces said folded portion.

12. The absorbent article according to claim 11, wherein
a lower end portion of said folded portion is included in said at least three sheet members in said second waist circumferential region.

13. The absorbent article according claim 1, wherein
said first waist circumferential region in said vertical direction has a width at least half a width of said waist circumferential region in said vertical direction.

14. The absorbent article according claim 1, wherein
said second waist elastic member includes a plurality of elastic threads, and
at least a portion of said plurality of elastic threads are disposed between an outermost sheet member and a sheet member that faces said outermost sheet member among said at least three sheet members in said second waist circumferential region.

15. The absorbent article according to claim 14, wherein
another portion of said plurality of elastic threads are disposed between two sheet members excluding said outermost sheet member among said at least three sheet members in said second waist circumferential region.

16. The absorbent article according to claim 1, wherein
said second waist elastic member is disposed between two sheet members excluding an outermost sheet member among said at least three sheet members in said second waist circumferential region,
said outermost sheet member and a sheet member that faces said outermost sheet member are not joined in said second waist circumferential region,
at least an upper end portion of said intermediate elastic member is disposed and joined between said outermost sheet member and said sheet member facing said outermost sheet member, in a lower portion of said waist circumferential region, and
a distance in said vertical direction between a lower end of said second waist elastic member and an upper end of said intermediate elastic member is 30 mm or less.

17. The absorbent article according to claim 1, wherein
said at least three sheet members in said second waist circumferential region includes:
an outermost sheet member;
an innermost sheet member; and
two sheet members sandwiched between said outermost sheet member and said innermost sheet member and having upper ends located at different positions in said vertical direction, and
said second waist elastic member includes a plurality of elastic threads,
a portion of said plurality of elastic threads being disposed between one of said outermost sheet member and said innermost sheet member and one of said two sheet members, and
another portion of said plurality of elastic threads being disposed between said one of said outermost sheet member and said innermost sheet member and the other of said two sheet members.

* * * * *